United States Patent [19]

Meanwell

[11] Patent Number: 5,362,879
[45] Date of Patent: Nov. 8, 1994

[54] 4-5-DIPHENYLOXAZOLE DERIVATIVES AS INHIBITORS OF BLOOD PLATELET AGGREGATION

[75] Inventor: Nicholas A. Meanwell, East Hampton, Conn.

[73] Assignee: Bristol-Myers Squibb Company, New York, N.Y.

[21] Appl. No.: 47,738

[22] Filed: Apr. 15, 1993

[51] Int. Cl.$^5$ .......................................... C07D 263/30
[52] U.S. Cl. ................................. 548/236; 514/374; 548/235
[58] Field of Search ................. 514/374; 548/236, 235

[56] References Cited

U.S. PATENT DOCUMENTS

| | | | |
|---|---|---|---|
| 3,578,671 | 5/1971 | Brown | 548/236 |
| 4,460,598 | 7/1984 | Lautenschlager et al. | 548/336 |
| 5,187,188 | 2/1993 | Meanwell | 514/374 |
| 5,254,576 | 10/1993 | Romine et al. | 514/374 |
| 5,262,540 | 11/1993 | Meanwell | 548/236 |

FOREIGN PATENT DOCUMENTS 0434034  6/1991  European Pat. Off.

OTHER PUBLICATIONS

Meanwell et al. (I) J. Med. Chem. vol. 35, pp 3483–3497 (1992).
Meanwell et al (II) J. Med. Chem. vol 35 pp 3498–3512 (1992).
Poplawski, et al., *J. Atherosclerosis Research*, 8: 721–723 (1968).
Lautenschlager, et al., *Drugs of the Future*, 11, 26–29 (1986).
Aldous, et al., *J. Org. Chem.*, 1151–1154 (1960).

Primary Examiner—Donald G. Daus
Attorney, Agent, or Firm—Prabodh I. Almaula

[57] ABSTRACT

A novel series of oxazole derivatives having the Formulae I and II wherein
R is H or $C_1$–$C_5$ lower alkyl,
X is N or CH,
Y is H or $CO_2R^1$, or $CO.R^2$, provided that when X is CH, Y is not H,
$R^1$ is $C_1$–$C_5$ lower alkyl, or phenylmethyl, and
$R^2$ is $C_1$–$C_5$ alkyl;

wherein
R is H or $C_1$–$C_5$ lower alkyl,
X is $(CH_2)_n$ or para or meta substituted phenyl wherein the substituent is $OR^2$,
$R^2$ is $C_1$–$C_5$ alkyl, and
n is an integer of 4 to 8, or a pharmaceutically acceptable salt thereof.

The compounds are useful as inhibitors of ADP-induced blood platelet aggregation in human platelet-rich plasma.

7 Claims, No Drawings

4-5-DIPHENYLOXAZOLE DERIVATIVES AS INHIBITORS OF BLOOD PLATELET AGGREGATION

BACKGROUND OF THE INVENTION

1. Field of the Invention

This invention relates to a series of novel oxazole derivatives which are useful as inhibitors of ADP-induced aggregation of human blood platelets in platelet-rich-plasma.

2. Description of the Art

Platelet aggregation is considered part of a complex physiological mechanism for formation of a thrombus in the vascular system. Thromboembolic phenomena, i.e., the formation of thrombi, are involved in hemostasis and a number of diseased states in mammals including thrombophlebitis, phlebothrombosis, cerebral thrombosis, coronary thrombosis and retinal vessel thrombosis. An increase in propensity for platelet aggregation, sometimes referred to as platelet adhesiveness, is observed following parturition, surgical operations such as coronary artery bypass surgery, organ transplant, angioplasty, prosthetic heart valve implants to name a few; and in ischemic heart disease, atherosclerosis, multiple sclerosis, intracranial tumors, thromboembolism, and hyperlipemia (A. Poplawski, et al, *J. Atherosclerosis Research*, 8:721 (1968)).

Octimibate (i) is a broad spectrum inhibitor of platelet aggregation; $IC_{50}=1$ μg/ml (human PRP vs ADP). (a. U.S. Pat. No. 4,460,598 b. Lautenschlager, et al., *Drugs of the Future*, 11, 26 (1986)).

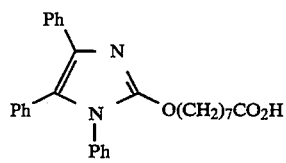

EPO 0434034, to Meanwell, et al., discloses (ii), which is an orally active broad spectrum inhibitor of platelet aggregation.

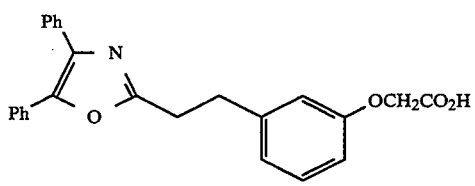

Lautenschlager, et al., U.S. Pat. No. 4,460,598 issued Jul. 17, 1984 describe a series of triphenylimidazol-2-yloxyalkanoic acids having the formula (iii)

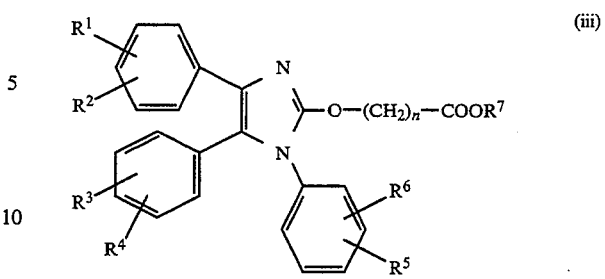

wherein $R^1$, $R^2$, $R^3$, $R^4$, $R^5$ and $R^6$ each are H, halogen alkyl, alkoxy and trifluoromethyl; n is an integer of 1 to 10 and $R^7$ is H, alkali metal ions, alkyl or benzyl group. The compounds of U.S. Pat. No. 4,460,598 are reportedly useful in the treatment of thromboembolic, inflammatory and/or atherosclerotic disease in man. A particularly preferred member of the series wherein $R^1$ to $R^6$ is hydrogen, n is 7 and $R^7$ is sodium (identified in the art as octimibate sodium) has been described as possessing anti-aggregatory activity.

Meanwhile, N. A., European Patent Application 0434034 further describes oxazole derivatives having formula (iv) or (v)

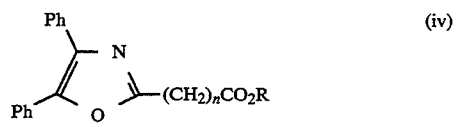

wherein n is 7-9 and R is hydrogen or lower alkyl

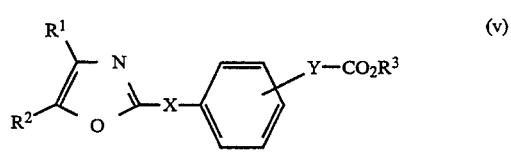

wherein $R^1$ and $R^2$ are each phenyl or thienyl; $R^3$ is hydrogen, lower alkyl or together with $CO_2$ is tetrazol-1-yl; X is a divalent connecting group; and Y is a divalent connecting group attached to the 3-or 4-phenyl position. Compounds of formulas (iv) and (v) are useful as inhibitors of mammalian blood platelet aggregation.

Among the compounds disclosed in the compounds of formula (vi) identified as

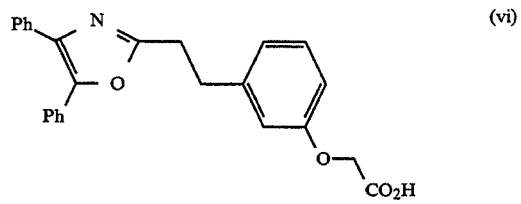

D. L. Aldous, et al., *J. Org. Chem.*, 1151 (1960) describe the chemistry of styryloxazoles of the formula (vii)

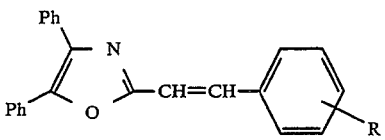

wherein R is hydrogen, p-methoxy, o-hydroxy and 3,4-methylendioxy.

Brown, U.S. Pat. No. 3,578,671 describes a class of oxazole-2-polycarbon aliphatic monocarboxylic acids arylated at the 4- and/or 5-position in the oxazole ring of the formula (viii)

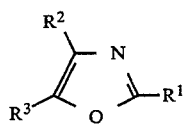

in which each of the substituents $R^2$ and $R^3$ is a member of the group consisting of unsubstituted phenyl, naphthyl, thienyl and furyl radicals and phenyl radicals substituted by substituents selected from the group consisting of halogen, lower alkyl, lower alkoxy, nitro and trifluoromethyl radicals; and wherein $R^1$ is selected from the group consisting of carboxyalklyl- and carboxylalkenyl radicals each containing from 2 to 5 carbon atoms and the amides, hydroxamic acid derivatives, lower alkyl esters and lower alkanoyloxy-lower-alkyl esters thereof. The compounds of U.S. Pat. No. 3,578,671 include the clinically effective anti-inflammatory agent known generically as oxaprozin ($R^2=R^3=$phenyl, $R^1=(CH_2)_2CO_2H$).

Meanwell, U.S. Pat. No. 5,187,188 describes compounds of the structure (ix)

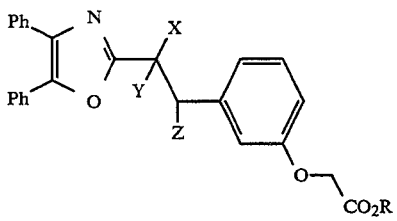

wherein Y and Z are independently hydrogen or together form a bond; X is CN, $CO_2R^1$ or $CO.NR^2R^3$; R and $R^1$ are independently or together H, Na, or $C_1$–$C_5$ lower alkyl; $R^2$ and $R^3$ are independently or together H, or $C_1$–$C_5$ lower alkyl.

SUMMARY OF THE INVENTION

The present invention provides novel oxazole derivatives having Formulae I and II, infra, and pharmaceutically acceptable salts thereof, which are useful as inhibitors of adenosine diphosphate-induced aggregation of human blood platelets in platelet rich plasma.

Another embodiment of the invention concerns pharmaceutical compositions comprised of a compound of Formulae I or II combined with at least one pharmaceutically acceptable excipient.

Yet another embodiment relates to a method for inhibiting blood platelet aggregation in a mammal which comprises administering a therapeutically effective amount of a compound of Formulae I or II to a mammal in need of such treatment.

DETAILED DESCRIPTION OF THE INVENTION

The present invention provides novel analogues of the compound of formula (ii) supra wherein the atom β-to the oxazole ring has been modified. In particular, the present invention is concerned with 4,5-diphenyloxazole derivatives having the Formulae I and II

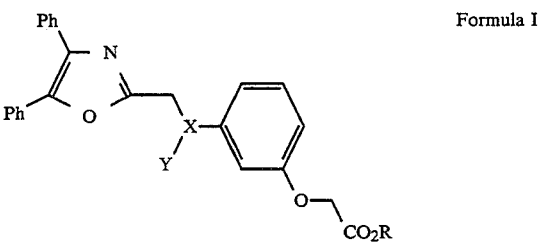

Formula I wherein
R is H or $C_1$–$C_5$ lower alkyl,
X is N or CH,
Y is H or $CO_2R^1$, or $CO.R^2$, provided that when X is CH, Y is not H,
$R^1$ is $C_1$–$C_5$ lower alkyl, or phenylmethyl, and
$R^2$ is $C_1$–$C_5$ alkyl;

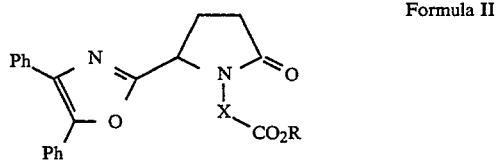

Formula II wherein
R is H or $C_1$–$C_5$ lower alkyl,
X is $(CH_2)_n$ or para or meta substituted phenyl wherein the substituent is $OR^2$,
$R^2$ is $C_1$–$C_5$ alkyl, and
n is an integer of 4 to 8,
and pharmaceutically acceptable salts thereof.

The compounds of Formula I and Formula II are useful as inhibitors of ADP-induced aggregation of human blood platelets in platelet rich plasma.

It is understood that as used herein limitations of Formulae I and II are defined as follows:

The term "$C_1$–$C_5$ lower alkyl" refers to a branched or unbranched saturated hydrocarbon chain containing from 1 to 5 carbon atoms, for example, methyl, ethyl, n-propyl, isopropyl, butyl, isobutyl, and 3-pentyl. The symbol "Ph" represents phenyl.

Also included within the scope of the present invention are the pharmaceutically acceptable metal salts and the solvates of the compounds of Formulas I and II which may exist in various tautomeric forms.

According to the present invention, the compounds characterized by Formulae I and II and the pharmaceutically acceptable acid addition salts thereof, were prepared as outlined in Schemes 1–4.

Scheme 1 depicts the synthetic approach to 8, the β-methoxycarbonyl analogue of the compound of formula (ii) supra. 3-Hydroxyphenylacetic acid (1) was esterified and the phenol protected as its 1-tertbutyldimethylsilyl(TBDMS)ether to give 2. The anion prepared from 2 by treatment with lithium diisopropylamide (LDA) in tetrahydrofuran (THF) at about −78° C., was alkylated with the bromomethyl oxazole 3 to provide adduct 4. Deprotection using fluoride furnished phenol 5 which was alkylated with methyl bromoacetate to give methyl ester 6. The acid 8 was obtained from 5 by alkylation with tert-butyl bromoacetate, to give ester 7, followed by dissolution in neat trifluoroacetic acid at about 0° C.

The acyclic β-amino analogues of the compound of formula (ii) were synthesized by the general route depicted in Scheme 2. 3-Nitrophenol (9) was alkylated with methyl bromoacetate and the nitro moiety reduced catalytically to provide the corresponding aniline 10. The nitrogen atom of 10 was derivatized with the appropriate acyl or carbonyl chloride to furnish the side chain precursor 11. The diphenyloxazole moiety was introduced by deprotonation of 11, using either sodium hydride (NaH) in N,N-dimethylformamide (DMF) or LDA in THF, followed by the addition of 2-bromomethyl-4,5-diphenyloxazole (3) to give the adducts 12. Saponification of 12 afforded the target acids 13. The parent structure 15 was synthesized from 12b (R=PhCH₂) by deprotection using H₂ over palladium on carbon to furnish ester 14 and subsequent alkaline hydrolysis to provide the acid 15.

The cyclic amides 19 and 20 were obtained as shown in Scheme 3. Condensation of benzoin (16) with pyroglutamic acid (17) followed by heating the crude material with excess ammonium acetate in acetic acid provided the oxazole 18. The amide nitrogen of 18 was deprotonated using NaH in DMF and alkylated with an ω-bromo ester to furnish the esters 19. Hydrolysis of 19 with lithium hydroxide in aqueous methanol gave acids 20.

The phenylated cyclic amides 26 and 27 were synthesized using the route outlined in Scheme 4. Reductive amination of α-ketoglutaric acid (22) with 3-aminophenol (21), using sodium cyanoborohydride (NaBH₃CN) in methanol, followed by acidification with concentrated sulfuric acid ($H_2SO_4$) and heating at reflux, provided the ester 23 in over 80% yield. Hydrolysis of 23 with lithium hydroxide gave the acid 24 which was alkylated with desyl bromide and cyclized to the oxazole 25 under standard conditions. Alkylation of the phenol of 25 with methyl bromoacetate afforded ester 26 which was saponified to the acid 27 using lithium hydroxide in aqueous methanol.

Scheme 1

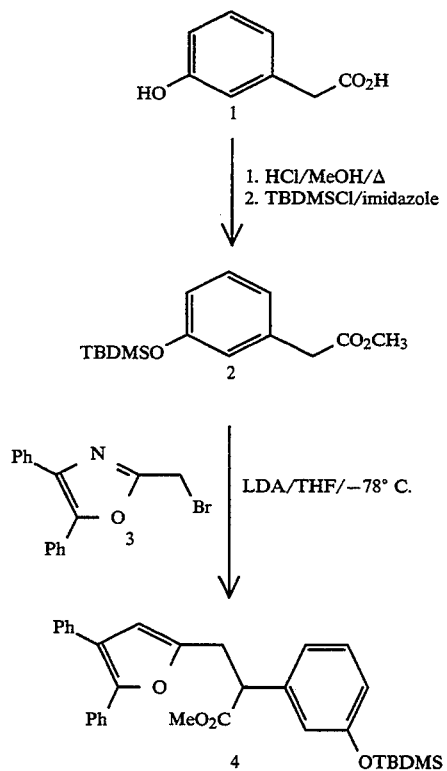

-continued
Scheme 1
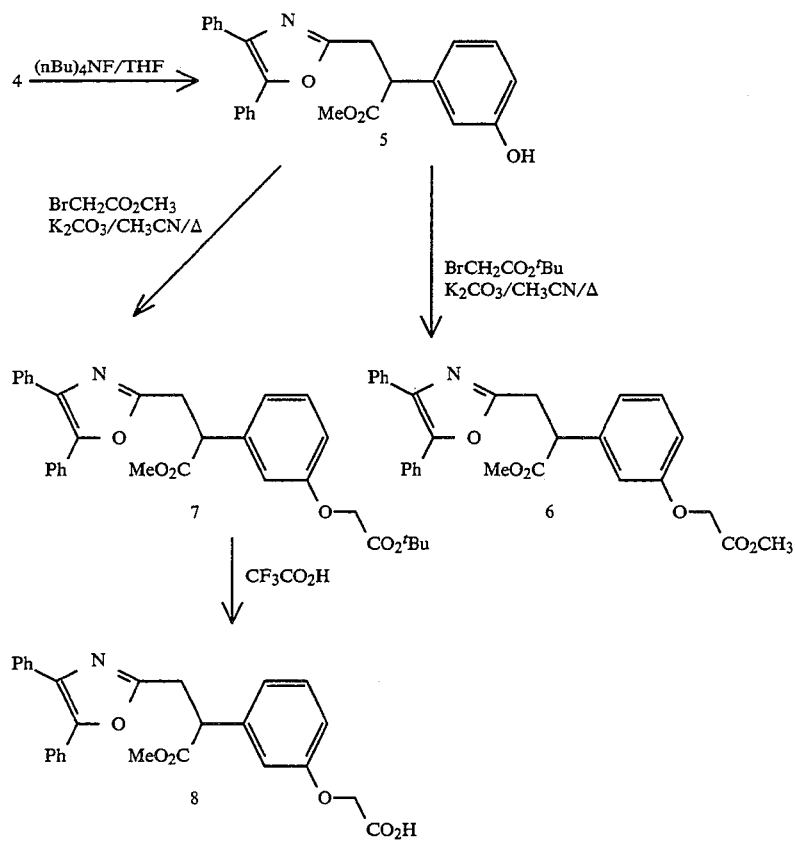
Scheme 2
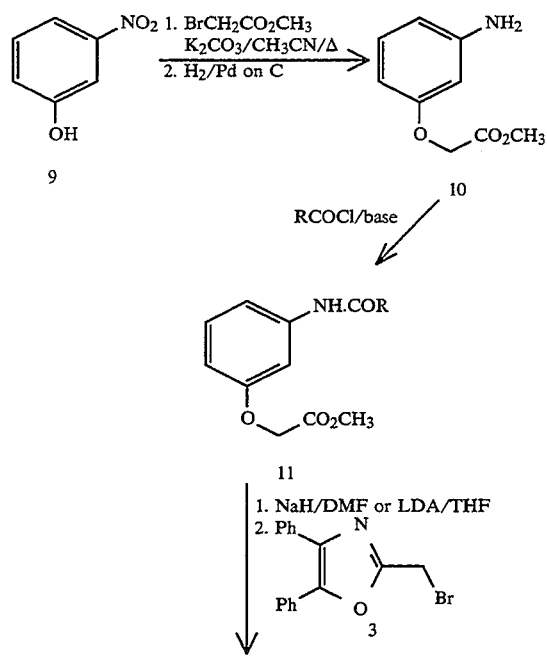

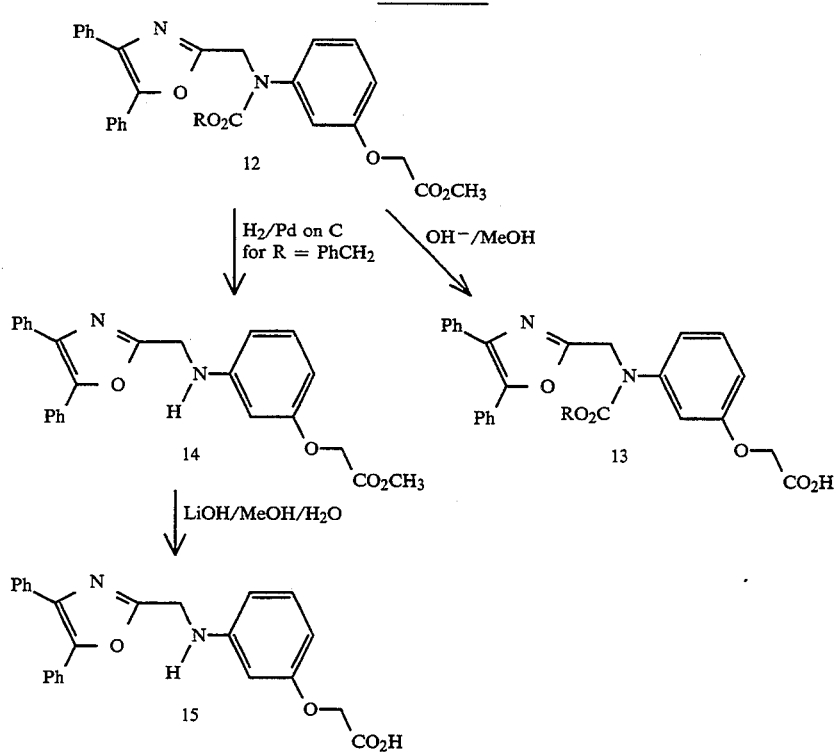
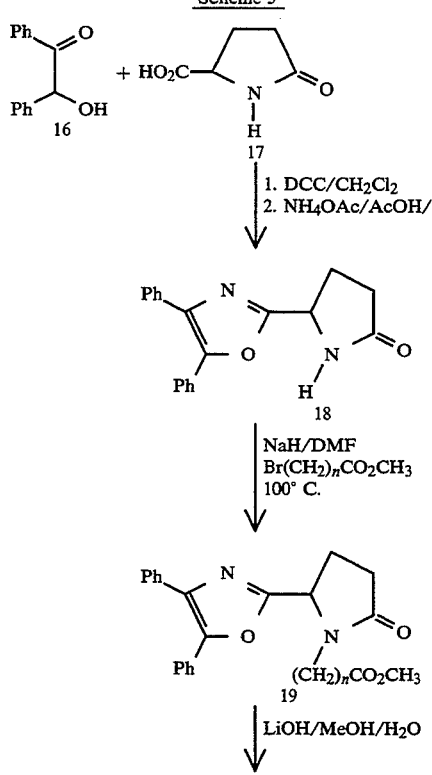
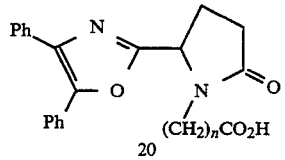
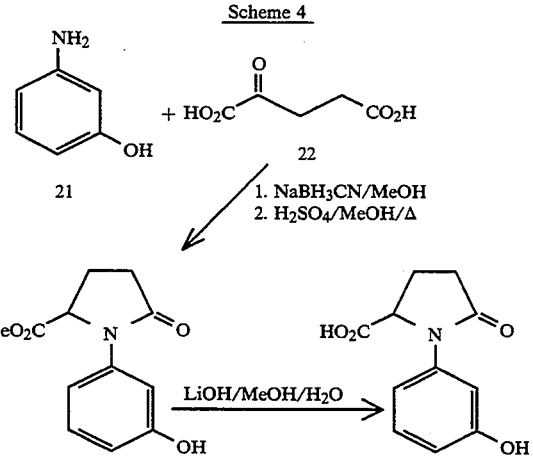

-continued
Scheme 4

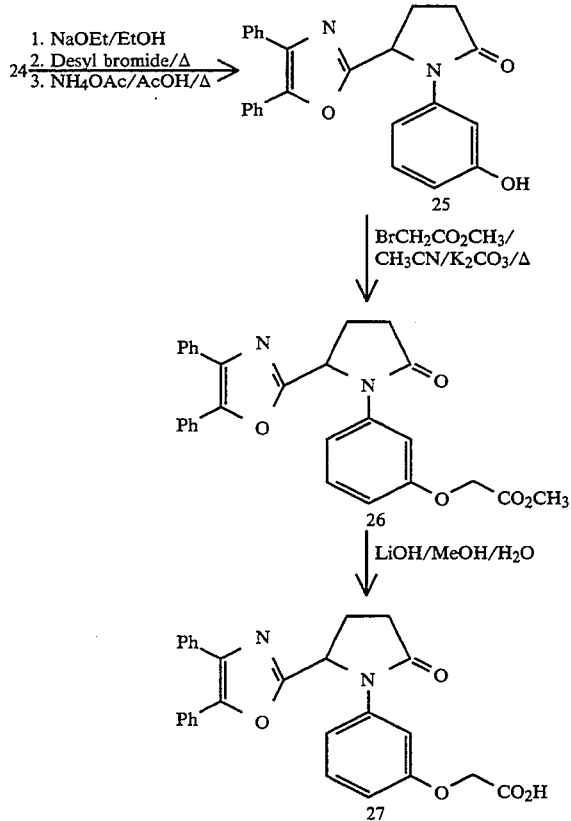

The compounds prepared as part of this study are listed in Table 1 along with relevant physical properties.

TABLE 1

| Compound No. | Mol. Formula | m p (°C.) |
| --- | --- | --- |
| 6 | $C_{28}H_{25}NO_6 \cdot 0.26H_2O$ | oil |
| 8 | $C_{27}H_{23}NO_6 \cdot 0.16H_2O$ | 106–108 |
| 14 | $C_{25}H_{22}N_2O_4$ | resin |
| 15 | $C_{24}H_{20}N_2O_4 \cdot 0.2H_2O$ | 146–151 |
| 12a | $C_{27}H_{24}N_2O_5$ | oil |
| 13a | $C_{26}H_{22}N_2O_5 \cdot 0.25H_2O$ | 75–80 |
| 12b | $C_{33}H_{28}N_2O_6 \cdot 0.3H_2O$ | resin |
| 13b | $C_{32}H_{26}N_2O_6 \cdot 0.5H_2O$ | resin |
| 12c | $C_{27}H_{24}N_2O_6 \cdot 0.4H_2O$ | oil |
| 13c | $C_{26}H_{22}N_2O_6 \cdot 0.5H_2O$ | 153–154 |
| 12d | $C_{28}H_{26}N_2O_6 \cdot 0.11H_2O$ | oil |
| 13d | $C_{27}H_{24}N_2O_6 \cdot 0.4H_2O$ | resin |
| 12e | $C_{29}H_{28}N_2O_6 \cdot 0.6H_2O$ | oil |
| 13e | $C_{28}H_{26}N_2O_6 \cdot 0.34H_2O$ | foam |
| 12f | $C_{29}H_{28}N_2O_6 \cdot 0.88H_2O$ | oil |
| 13f | $C_{28}H_{26}N_2O_6 \cdot 0.4H_2O$ | foam |
| 19a | $C_{27}H_{30}N_2O_4 \cdot 0.175H_2O$ | oil |
| 20a | $C_{26}H_{28}N_2O_4 \cdot 0.3CH_2Cl_2$ | oil |
| 19b | $C_{28}H_{32}N_2O_4 \cdot 0.19H_2O$ | oil |
| 20b | $C_{27}H_{30}N_2O_4 \cdot 0.21CH_2Cl_2$ | oil |
| 26 | $C_{28}H_{24}N_2O_5$ | resin |
| 27 | $C_{27}H_{22}N_2O_5 \cdot 0.3H_2O \cdot 0.2C_6H_{14}$ | 75–90 |

Biological Activity

Blood Platelet Aggregometry.

Platelet-rich plasma was prepared from human blood drain into syringes containing 1/10 volume of 3.8% sodium citrate. The blood was then subjected to centrifugation for about 10 minutes at 140 g and then the platelet-rich plasma decanted. The test compound was dissolved in DMSO (5 μL) and added to PRP (0.9 mL) 3 minutes prior to the addition of ADP (5.86 μM). The aggregometer method of Born, as modified by Mustard et al., was employed to measure platelet aggregation. Vehicle control trials were performed and compared with the extent of aggregation induced in PRP containing various concentrations of the test compounds. Dose-response curves were thus obtained and $IC_{50}$ values determined. The data presented in Table I are the results of single determinations of the average of duplicates. Rabbit and rat PRP were prepared in a similar fashion, and ADP in a final concentration of 29.3 μM was employed as the agonist.

The target compounds were evaluated as inhibitors of ADP-induced aggregation of human platelets in platelet-rich-plasma and the results are presented in Table 2. For comparison purposes, the $IC_{50}$ for the compound of Formula (ii) supra, is 0.6 mg/mL.

From the data presented in Table 2 it is apparent that substitution at the position β- to the oxazole ring of the compound of Formula (ii) imparts significant influence on biological activity and potency, which influence results in a significant increase in biological activity. For example, the compound 13d inhibits ADP-induced platelet aggregation with an $IC_{50}$ of 0.15 mg/mL and is four times as potent as the compound of Formula (ii).

TABLE 2

| Biological activity of synthetic compounds | |
| --- | --- |
| Compound No. | $IC_{50}$ vs ADP Human PRP, mg/mL |
| 6 | 9 |
| 8 | 16 |
| 14 | 1.8 |
| 15 | 1.2 |
| 12a | 1.5 |
| 13a | 2.5 |
| 12b | >32 |
| 13b | 30 |
| 12c | 0.59 |
| 13c | 0.69 |
| 12d | 0.03 |
| 13d | 0.15 |
| 12e | 0.1 |
| 13e | 0.18 |
| 12f | 0.22 |
| 13f | 0.14 |
| 19a | 3.2 |
| 20a | 0.12 |
| 19b | >32 |
| 20b | 5 |
| 26 | 7.0 |
| 27 | 2.6 |
| Compound of Formula (ii) | 0.6 |

Thus, the Formulae I and II compounds and pharmaceutically acceptable salts thereof have pharmacological properties which make them particularly useful as inhibitors of ADP-induced aggregation of human blood platelets in platelet rich plasma.

Another embodiment of the invention concerns pharmaceutical compositions comprised of a Formulae I or II compound or metal salts thereof combined with at least one pharmaceutically acceptable carrier or excipient. Yet another embodiment relates to a method for inhibiting blood platelet aggregation in a mammal which comprises administering a therapeutically effective amount of a compound of Formulae I or II to a mammal in need of such treatment.

The dosage employed in the instant therapeutic methods will vary with the form of administration, the particular compound chosen, the subject being tested and the effect desired. Suitable effective doses in animals range from 0.01 to 50 mg/Kg body weight orally and from 0.001 to 20 mg/kg body weight parenterally (generally characterized as subcutaneous, intramuscular, and intravenous injection). It is contemplated that the effective unit dose in man will range from 0.1 to 50 mg/Kg and preferably from 0.5 to 30 mg/Kg administered one to three times a day. In accordance with conventional clinical practice, the effective dose can be determined by administering a Formulae I or II compound at a dosage substantially less than the dose of the compound which is thought to be effective and then increasing the dosage in small increments until the desired effect is achieved.

In carrying out the instant therapeutic methods, the active ingredient of Formulae I or II and pharmaceutically acceptable acid addition salts thereof are preferably administered with a pharmaceutically acceptable carrier and such compositions constitute part of the instant invention. Suitable dosage forms for oral use are tablets, dispersible powders, granules, capsules, syrups and elixirs. Examples of parenteral forms are solutions, suspensions, dispersions, emulsions, and the like. The compositions for oral use may contain one or more conventional adjuvants, such as sweetening agents, flavoring agents, coloring agents and preserving agents, in order to provide a composition of suitable pharmaceutical elegance. Tablets may contain the active ingredient in admixture with conventional pharmaceutical acceptable excipients including inert diluents such as calcium carbonate, sodium carbonate, lactose and talc; granulating and disintegrating agents such as starch and alginic acid; binding agents such as starch, gelatin and acacia and lubricating agents such as magnesium stearate, stearic acid and talc. The tablets may be uncoated by known techniques to delay disintegration and absorption in the gastrointestinal tract and thereby provide a sustained action over a longer period. Similarly, suspension, syrups and elixirs may contain the active ingredient in admixture with any of the conventional excipients utilized for the preparation of such compositions such as suspending agents (e.g., methylcellulose, tragacanth, and sodium alginate), wetting agents (e.g., lecithin, polyoxyethylene stearate) and preservatives such as ethyl-p-hydroxybenzoate. Capsules may contain the active ingredient alone or admixed with an inert solid diluent such as calcium carbonate, calcium phosphate and kaolin. The injectable compositions are formulated as known in the art and may contain appropriate dispersing or wetting agents and suspending agents identical or similar to those mentioned above.

All publications cited in this specification are indicative of the level of skill of those skilled in the art to which this invention pertains. Each publication is individually incorporated herein by reference in the location where it is cited.

The compounds which constitute the invention and their methods of preparation will appear more fully from a consideration of the following examples. The compounds which are not shown by specific example are readily prepared by analogous procedure. The following examples are given by way of illustration and are not to be construed as limiting the invention in any way inasmuch as many variations of the invention are possible within the spirit of the invention.

All temperatures are degrees Centigrade and melting points taken with a Thomas Hoover capillary apparatus are uncorrected. Conventional abbreviations are employed in reporting Nuclear Magnetic Resonance (NMR) spectral data with tetramethylsilane as internal reference and chemical shift data values in parts per million.

EXAMPLE 1

Methyl α-[3-[(methoxycarbonyl)methoxy]phenyl-4,5-diphenyl-2-oxazolepropanoate (6)

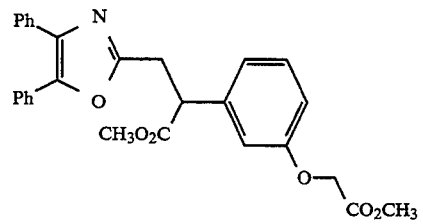

A solution of methyl 3-[[(1,1-dimethylethyl)dimethylsilyl]oxy]benzeneacetate (12.00 g, 43 mmol) in dry THF (40 mL) was added dropwise to a solution of LDA (prepared from nBuLi (20.70 mL of a 2.5 M solution, 3.32 g, 51 mmol) and $^i$Pr$_2$NH (4.79 g, 6.60 mL, 47 mmol)) in THF (300 mL) maintained at about $-78°$ C. under an atmosphere of N$_2$. After about 15 minutes, 2-bromomethyl-4,5-diphenyloxazole (14.86 g, 47 mmol) in THF (20 mL) was added dropwise. The mixture was stirred for about 30 minutes at about $-78°$ C., poured onto saturated NH$_4$Cl solution and extracted with CH$_2$Cl$_2$. The combined extracts were dried over Na$_2$SO$_4$, concentrated and the residual oil chromatographed on a column of silica gel. Elution with a mixture of hexanes and Et$_2$O (9:1) gave methyl α-[3-[[(1,1-dimethylethyl)dimethylsilyl]oxy]phenyl]-4,5-diphenyl-2-oxazolepropanoate (12.40 g, 56%) $^1$H NMR (CDCl$_3$) δ0.18 (6H, s, Si(CH$_3$)2), 0.98 (9H, s, (CH$_3$)$_3$C), 3.23 and 3.65 (2H, d of ABq, J=16 Hz, J'=8 Hz, CH$_2$-oxazole), 3.72 (3H, s, CO$_2$CHH$_3$), 4.29 (1H, dd, J=8 Hz, CHCO$_2$CH$_3$), 6.77 (1H, d, J=9 Hz, aromatic H), 6.88 (1H, s, aromatic H), 6.98 (1H, d, J=9 Hz, aromatic H), 7.20 (1H, t, J=8Hz, aromatic H), 7.25 to 7.45 (6H, m, aromatic H), 7.45 to 7.70 (4H, m, aromatic H).

A solution of nBu4NF (7.30 g, 28 mmol) in dry THF (27.9 mL) was added to a solution of methyl α-[3-[[(1,1-dimethylethyl)dimethylsilyl]oxy]phenyl]-4,5-di phenyl-2-oxazolepropanoate (11.90 g, 23 mmol) in dry THF (250 mL) maintained at about $-78°$ C. under an atmosphere of N$_2$. After about 10 minutes, the mixture was poured onto saturated NH$_4$Cl solution and extracted with CH$_2$C$_2$. The combined extracts were dried over Na$_2$SO$_4$, concentrated and the residue chromatographed on a column of silica gel. Elution with a mixture of Et$_2$O and hexanes (1:1) gave methyl α- (3-hydroxyphenyl)-4,5-diphenyl-2-oxazolepropanoate (4.59 g, 47%).

A mixture of methyl α-(3-hydroxyphenyl)-4,5-diphenyl-2-oxazolepropanoate (1.00 g, 2.5 mmol), methyl bromoacetate (422 mg, 0.26 mL, 2.75 mmol), K$_2$CO$_3$ (415 mg, 3 mmol) and CH$_3$CN (20 mL) was heated at reflux for about 45 minutes. The mixture was cooled, filtered and concentrated and the residue subjected to chromatography on a column of silica gel. Elution with a mixture of hexanes and Et$_2$O (3:2) gave methyl α-[3-[(methoxycarbonyl)methoxy]phenyl-4,5-diphenyl-2-oxazolepropanoate (1.10 g, 93%). IR (Film) 1750

($CO_2CH_3$) cm$^{-1}$; $^1$H NMR (CDCl$_3$) δ3.22 and 3.66 (1H, d of ABq, J=16 Hz, J'=8 Hz, CH$_2$-oxazole), 3.70 (3H, s, CO$_2$CH$_3$), 3.79 (3H, s, CO$_2$CH$_3$), 4.30 (1H, dd, J=8 Hz, CHCO$_2$CH$_3$), 4.61 (2H, s, OCH$_2$CO$_2$CH$_3$), 6.82 (1H, dd, J=8 Hz, J'=2.5 Hz, aryl H ortho to 0), 6.95 (1H, d, J=2.5 Hz, aryl H ortho to 0), 7.01 (1H, d, J=8 Hz, aryl H para to 0), 7.20–7.45 (7H, m, aromatic H), 7.50–7.70 (4H, m, aromatic H); MS m/z 472 (MH+).

Anal. calcd for C$_{28}$H$_{25}$NO$_6$·0.26H$_2$O:
C, 70.63; H, 5.40; N, 2.94; H$_2$O, 0.98.
Found: C, 70.63; H, 5.30; N, 3.22; H$_2$O, 0.16.

EXAMPLE 2

Methyl α-[3-[[(1,1-dimethylethoxy)carbonyl]methoxy]phenyl-4,5-diphenyl-2-oxazole-propanoate (7)

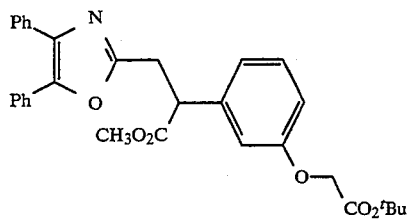

A mixture of methyl α-(3-hydroxyphenyl)-4,5-diphenyl-2-oxazolepropanoate (2.00 g, 5 mmol), tertbutyl bromoacetate (1.08 g, 0.88 mL, 5.5 mmol), K$_2$CO$_3$ (760 mg, 5.5 mmol) and CH$_3$CN (40 mL) was heated at reflux for about 45 minutes. After about 1 hour, the mixture was cooled, filtered and concentrated to leave an oil. Chromatography on a column of silica gel using a mixture of hexanes and Et$_2$O (3:1) as eluent gave methyl α-[3-[[(1,1-dimethylethoxy) carbonyl]methoxy]phenyl-4,5-diphenyl-2-oxazolepropanoate (2.60 g, 100%). IR (Film) 1750 (CO$_2$$^t$Bu+CO$_2$CH3) cm$^{-1}$; $^1$H NMR (CDCl$_3$) δ1.48 (9H, s, (CH$_3$)$_3$C), 3.20 and 3.66 (1H, d of ABq, J=15 Hz, J'=6 Hz, CH$_2$-oxazole), 3.69 (3H, s, CO$_2$CH$_3$), 4.29 (1H, dd, J=6 Hz, CHCO$_2$CH$_3$), 4.50 (2H, s, OCH$_2$CO$_2$$^t$Bu), 6.82 (1H, dd, J=9 Hz, J'=2 Hz, aryl H ortho to 0), 6.93 (1H, d, J=2 Hz, aryl H ortho to 0), 6.99 (1H, d, J=9 Hz, aryl H para to 0), 7.25–7.45 (7H, m, aromatic H), 7.50–7.65 (4H, m, aromatic H); MS m/z 514 (MH+).

Anal. calcd for C$_{31}$H$_{31}$NO$_6$:
C, 72.50; H, 6.08; N, 2.73.
Found: C, 72.35; H, 6.04; N, 2.94.

EXAMPLE 3

Methyl α-[3-(carboxymethoxy)phenyl-4,5-diphenyl-2-oxazole-propanoate (8)

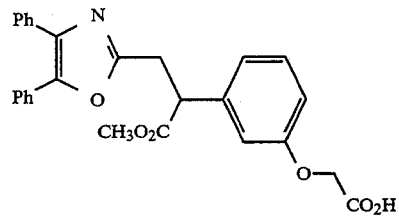

Ice cold CF$_3$CO$_2$H (25 mL) was added to methyl α-[3[[(1,1-dimethylethoxy)carbonyl]methoxy]phenyl-4,5-diphenyl-2-oxazolepropanoate (2.30 g, 4.5 mmol) and the mixture stirred at about 0° C. for about 2 hours. The mixture was concentrated in vacuo, the residue diluted with H$_2$O and extracted with CH$_2$Cl$_2$. The combined extracts were dried over Na$_2$SO$_4$ and the solvent evaporated to leave a foam which was dissolved in Et$_2$O and diluted with hexanes to give methyl α-[3-(carboxymethoxy)phenyl-4,5-diphenyl-2-oxazolepropanoate (1.90 g, 93%), mp 106–108° C. IR (KBr) 3600–2700 (CO$_2$H), 1740 (CO$_2$CH$_3$) 1730 (CO$_2$H) cm$^{-1}$; $^1$H NMR (CDCl$_3$) δ3.31 and 3.65 (1H, d of ABq, J=15 Hz, J'=7 Hz, CH$_2$-oxazole), 3.69 (3H, s, CO$_2$CH$_3$), 4.29 (1H, t, J=7 Hz, CHCO$_2$CH$_3$), 4.62 (2H, s, OCH$_2$CO$_2$H), 6.83 (1H, dd, J=9Hz, J'=2 Hz, aryl H ortho to 0), 6.97 (2H, m, aryl H ortho and para to 0), 7.20–7.50 (7H, m, aromatic H), 7.52–7.60 (4H, m, aromatic H); MS m/z 458 (MH+).

Anal. calcd for C$_{27}$H$_{23}$NO$_6$·0.16H$_2$O:
C, 70.44; H, 5.11; N, 3.04; H$_2$O , 0.63.
Found: C, 70.44; H, 5.14; N, 3.23; H$_2$O, 0.27.

EXAMPLE 4

Methyl 3-[N-[(4,5-diphenyl-2-oxazolyl)methyl]-N-[(phenylmethoxy) carbonyl]aminophenoxy]acetate (12b)

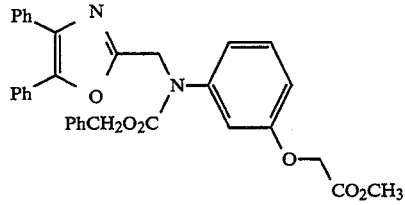

A solution of methyl [3-[[(phenylmethoxy)carbonyl]amino]phenoxy]acetate (4.39 g, 14 mmol) in dry THF (200 mL) was added dropwise to a solution of LDA (1.64 g, 15 mmol) in dry THF (20 mL) maintained at about −78° C. under an atmosphere of N$_2$. The mixture was warmed to about 0° C. stirred for about 5 minutes and cooled to about −78° C. before adding a solution of 2-bromomethyl-4,5-diphenyloxazole (4.38 g, 14 mmol) in THF (30 mL) dropwise. The mixture was allowed to warm to room temperature, stirred for about 16 hours and diluted with a mixture of Et$_2$O and saturated NH$_4$Cl solution. The organic phase was separated, washed with H$_2$O and saturated NaCl solutions dried over MgSO$_4$ and concentrated in vacuo. The residual oil was chromatographed on a column of silica gel using a mixture of hexanes and EtOAc (3:1) as eluent to give methyl 3-[N-[(4,5-diphenyl-2-oxazolyl)methyl]-N-[(phenylmethoxy)carbonyl]aminophenoxy]acetate (2.64 g, 34%) . IR (Film) 1750 (CO$_2$CH$_3$), 1715 (N—CO$_2$) cm$^{-1}$; $^1$H NMR (CDCl$_3$) δ3.71 (3H s, CO$_2$CH$_3$), 4.72 (2H, s, OCH$_2$CO$_2$CH$_3$), 5.00 (2H, s, OCH$_2$), 5.20 (2H, s, oxazole-CH$_2$), 6.78 (1H, dd, J=9 Hz, J'=2 Hz, aromatic H), 7.00 (2H, bs, aromatic H), 7.20–7.40 (12H, m, aromatic H), 7.45–7.65 (4H, m, aromatic H); MS m/z 549 (MH+).

Anal. calcd for C$_{33}$H$_{28}$N$_2$O$_6$·0.3H$_2$O: C, 71.55; H, 5.21; N, 5.06; H$_2$O, 0.98. Found: C, 71.40; H, 4.84; N, 5.05; H$_2$O, 1.25.

EXAMPLE 5

3-[N-[(4,5-diphenyl-2-oxazolyl)
methyl]-N-[(phenylmethoxy) carbonyl
]aminophenoxy]acetic acid (13b)

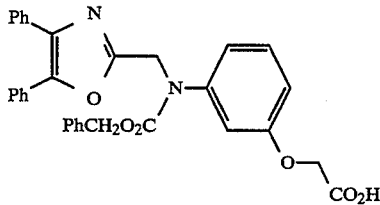

A mixture of methyl 3-[N-[(4,5-diphenyl-2oxazolyl) methyl]-N-[(phenylmethoxy)carbonyl]aminophenoxy]acetate (0.86 g, 1.6 mmol), LiOH.H$_2$O (67 mg, 1.6 mmol) and MeOH (20 mL) was stirred at room temperature for about 48 hours before being concentrated in vacuo. The residue was diluted with H$_2$O, acidified with 2N HCl solution and extracted with CH$_2$Cl$_2$. The combined extracts were washed with H$_2$O and saturated NaCl solution, dried over MgSO$_4$ and concentrated to give 3-[N-[(4,5-diphenyl-2oxazolyl)methyl]-N-[(phenylmethoxy)carbonyl]aminophenoxy]acetic acid (0.73 g, 86%). IR (KBr) 3600-2300 (CO$_2$H), 1720 (CO$_2$H, N-CO$_2$) cm$^{-1}$; $^1$H NMR (CDCl$_3$) δ4.54 (2H, s, OCH$_2$CO$_2$H), 5.11 (2H, s, OCH$_2$), 5.27 (2H, s, oxazole-CH$_2$), 6.84 (1H, d, J=9 Hz, aromatic H), 7.00 (2H, bs, aromatic H), 7.10-7.40 (12H, m, aromatic H), 7.50-7.65 (4H, m, aromatic H); MS m/z 535 (MH+).

Anal. calcd for C$_{32}$H$_{26}$N$_2$O$_6$. 0.5H$_2$O: C, 70.71; H, 5.01; N, 5.16; H$_2$O, 1.66. Found: C, 70.31; H, 4.83; N, 5.05; H$_2$O, 1.24.

EXAMPLE 6

Methyl 3-[[(4,5-diphenyl-2-oxazolyl)methyl
]amino]phenoxy]acetate (14)

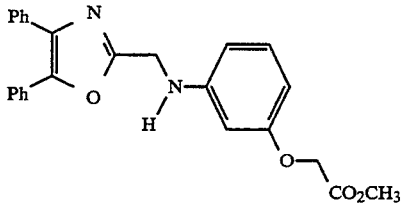

A solution of methyl 3-[N-[(4,5-diphenyl-2oxazolyl)-methyl]-N-[(phenylmethoxy)carbonyl]aminophenoxy]acetate (1.49 g, 2.7 mmol) in EtOAc (125 mL) was hydrogenated over 10% Pd on C (0.78 g) at 50 psi in a Parr hydrogenation apparatus. After hydrogen uptake had ceased, the mixture was filtered through Celite, concentrated and the residue chromatographed on a column of silica gel. Elution with a mixture of hexanes and EtOAc (3:1) gave methyl 3-[[(4,5-diphenyl-2-oxazolyl)methyl]amino]phenoxy]acetate (0.78 g, 69%). IR (NaCl) 1750 (CO$_2$CH$_3$) cm$^{-1}$; $^1$H NMR (CDCl$_3$) δ3.79 (3H, s, CO$_2$CH$_3$), 4.50 (2H, bs, CH$_2$N), 4.53 (1H, bs, NH), 4.61 (2H, s, OCH$_2$), 6.30 (1H, dd, J=9 Hz, J'=2 Hz, aromatic H ortho to O and N), 6.37 (1H, t, J=2 Hz, aromatic H), 6.43 (1Ht dd, J=9 Hz, J'=2Hz, aromatic H), 7 12 (1H, t, J=7 Hz, aromatic H), 7.35-7.45 (6H, m, aromatic M), 7.50-7.70 (4H, m, aromatic H); MS m/z 4 15 (MH+).

Anal. calcd for C$_{25}$H$_{22}$N$_2$O$_4$: C, 72.46; H, 5.36; N, 6.76. Found: C, 72.19; H, 5.22; N, 6.61.

EXAMPLE 7

[3
-[[(4,5-diphenyl-2-oxazolyl)methyl]amino]phenoxy]acetic acid (15)

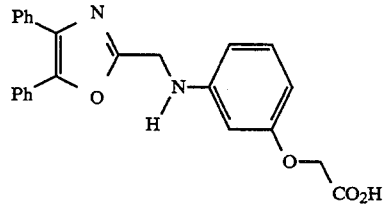

A mixture of methyl 3-[[(4,5-diphenyl-2-oxazolyl)methyl]amino]phenoxy]acetate (0.46 g, 1.1 mmol), LiOH.H$_2$O (90 rag, 2.2 mmol) and MeOH (20 mL) was stirred at room temperature for about 45 hours. The mixture was poured onto saturated NH$_4$Cl solution and extracted with EtOAc to give a foam which was diluted with 1N HCl solution and extracted with CH$_2$Cl$_2$. The organic phase was washed with H$_2$O and saturated NaCl solution, dried over MgSO$_4$ and concentrated to give [3-[[(4,5-diphenyl-2 -oxazolyl)methyl]amino]phenoxy]acetic acid (0.45 g, 100%), mp 146-151° C. IR (KBr) 1750 (CO$_2$H) cm$^{-1}$; $^1$H NMR (CDCl$_3$) δ4.25 (2H, bs, CO$_2$H, NH), 4.39 (2H, s, CH$_2$), 4.46 (2H, s, CH$_2$), 6.15 to 6.35 (3H, m, aromatic H), 6.99 (1H, t, J=8 Hz, aromatic H), 7.20-7.30 (6H, m, aromatic H), 7.40-7.55 (4H, m, aromatic H); MS m/z 401 (MH+).

Anal. calcd for C$_{24}$H$_{20}$N$_2$O$_4$.0.2H$_2$O: C, 71.35; H, 5.09; N, 6.94. Found: C, 71.00; H, 5.00; N, 6.62.

EXAMPLE 8

Methyl [3-[N-acetyl-[(4,5-diphenyl-2-oxazolyl)methyl
]aminolphenoxy]acetate (12a)

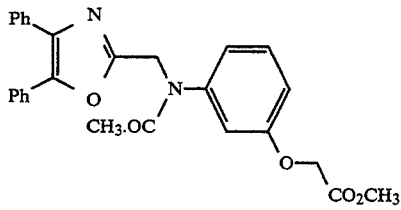

A solution of methyl [3-(acetylamino)phenoxy]acetate (1.00 g, 4.5 mmol) in dry THF (20 mL) was added dropwise to a solution of LDA (0.53 g, 5 mmol) in dry THF (5 mL) maintained at about −78° C. under an atmosphere of N$_2$. The mixture was warmed to about 0° C. and stirred about 5 minutes, cooled to about −78° C. and a solution of 2-bromomethyl-4,5-diphenyloxazole (1.41 g, 4.5 mmol) in THF (10 mL) added dropwise. The solution was allowed to warm to room temperature, stirred for about 18 hours and diluted with a mixture of saturated NH$_4$Cl solution and Et$_2$O. The organic phase was separated, washed with H$_2$O and saturated NaCl solution, and dried over MgSO$_4$. The solvent was evaporated and the residue chromatographed on a column of silica gel using a mixture of EtOAc and hexanes (13:7) as eluent to give methyl [3-[N-acetyl-[(4,5-diphenyl-2-oxazolyl)methyl]amino]phenoxy]acetate (0.85 g, 42%). IR (Film) 1750 (CO$_2$CH$_3$), 1670 (NCOCH$_3$)

cm⁻¹; ¹H NMR (CDCl₃) δ1.92 (3H, s, COC$\underline{H}_3$), 3.70 (3H, s, CO₂C$\underline{H}_3$), 4.55 (2H, s, OC$\underline{H}_2$), 5.10 (2H, s, NC$\underline{H}_2$) 6.75–6.95 (3H, m, aromatic $\underline{H}$), 7.20–7.40 (7H, m, aromatic $\underline{H}$), 7.45–7.60 (4H, m, aromatic $\underline{H}$); MS m/z 457 (MH⁺).

Anal. calcd for C₂₇H₂₄N₂O₅: C, 71.05; H, 5.30; N, 6.14. Found: C, 71.06; H, 5.11; N, 6.01.

EXAMPLE 9

[3-[N-acetyl-[(4,5-diphenyl-2oxazolyl)methyl]amino]-phenoxy]acetic acid (13a)

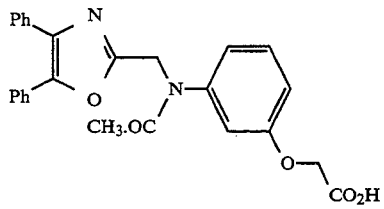

A mixture of methyl [3-[N-acetyl-[(4,5-diphenyl-2-oxazolyl)methyl]amino]phenoxy]acetate (0.58 g, 1.3 mmol), LiOH.H₂O (0.05 g, 1.3 mmol) and MeOH (30 mL) was stirred at room temperature for about 15 hours before adding LiOH.H₂O (0.05 g, 1.3 mmol). After about 1 hour, the solvent was evaporated, the residue diluted with 1N HCl solution and extracted with CH₂Cl₂. The combined extracts were washed with saturated NaCl solution, dried over MgSO₄ and concentrated in vacuo to leave [3-[N-acetyl-[(4,5-diphenyl-2-oxazolyl) methyl]amino]phenoxy]acetic acid (0.51 g, 91%), mp 75–80° C. IR (KBr) 2500 (CO₂H), 1740 (CO₂H), 1660 (NCOCH₃) cm⁻¹; ¹H NMR (CDCl₃) δ1.95 (3H, s, COC$\underline{H}_3$), 4.55 (2H, s, OC$\underline{H}_2$), 5.11 (2H, s, NC$\underline{H}_2$) 6.70–6.95 (3H, m, aromatic $\underline{H}$) , 7.25–7.40 (7H, m, aromatic $\underline{H}$) , 7.45–7.65 (4H, m, aromatic $\underline{H}$); MS m/z 443 (MH⁺).

Anal. calcd for C₂₆H₂₂N₂O₅0.25H₂O: C, 69.87; H, 5.08; N, 6.27; H₂O, 1.01. Found: C, 70.02; H, 4.88; N, 6.00; H₂O , 1.14.

EXAMPLE 10

Methyl [3-[[(4,5-diphenyl-2-oxazolyl)methyl](methoxycarbonyl)amino]phenoxy]acetate (12c)

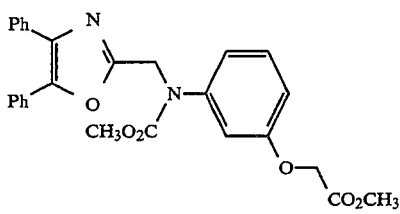

NaH (0.34 g of a 50% dispersion in mineral oil, 3.5 mmol) was washed twice with hexanes and covered with dry THF (10 mL). A solution of methyl [3-[(methoxycarbonyl)amino]phenoxy]acetate (0.75 g, 3 mmol) in dry THF (10 mL) was added and the mixture stirred at room temperature. After about 30 minutes, a solution of 2-bromomethyl-4,5-diphenyl-oxazole (0.99 g, 3 mmol) in THF (7 mL) was added and the mixture stirred overnight at room temperature. The mixture was diluted with saturated NH₄Cl solution and Et₂O, the organic phase separated, washed with H₂O and saturated NaCl solution and dried over MgSO₄. The solvent was evaporated and the residue chromatographed on a column of silica gel using a mixture of hexanes and EtOAc (4:1) as eluent to give methyl [3-[[(4,5-diphenyl-2-oxazolyl)methyl](methoxycarbonyl) amino]phenoxy]acetate (0.71 g, 48%). IR (film) 1760, (CO₂CH₃), 1715 (NCO₂CH₃) cm⁻¹; ¹H NMR (CDCl₃) δ3.73 (6H, s, CO₂C$\underline{H}$3), 4.58 (2H, s, OC$\underline{H}_2$CO₂CH₃), 4.99 (2H, s, C$\underline{H}_2$-oxazole), 6.79 (1H, dd, J=9 Hz, J'=2 Hz, aromatic $\underline{H}$), 7.02 (2H, m, aromatic $\underline{H}$), 7.20 to 7.45 (7H, m, aromatic $\underline{H}$), 7.50 to 7.65 (4H, m, aromatic $\underline{H}$); MS m/z 473 (MH⁺).

Anal. calcd. for C₂₇H₂₄N₂O₆.0.4H₂O: C, 67.60; H, 5.21, N, 5.84; H₂O, 1.50. Found: C, 67.69; H, 4.95; N, 5.59; H₂O , 3.07%.

EXAMPLE 11

[3-[[(4,5-diphenyl-2-oxazolyl)methyl](methoxycarbonyl)amino]phenoxy]acetic acid (13c)

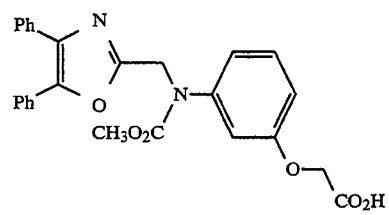

A mixture of methyl [3-[[(4,5-diphenyl-2-oxazolyl)-methyl](methoxycarbonyl) amino]phenoxy]acetate (4.16 g, 9 mmol), LiOH.H₂O (0.56 g, 13 mmol), MeOH (45 mL) and H₂O (15 mL) was stirred at room temperature for about 3 hours. The solvent was removed in vacuo, the residue diluted with H₂O and 2N HCl until pH=2 and a yellow solid filtered off. Recrystallization from a mixture of CH₂Cl₂ and hexanes gave [3-[[(4,5-diphenyl-2-oxazolyl)methyl](methoxycarbonyl)amino]-phenoxy]acetic acid (2.25 g, 55%), mp 153–155° C. IR (KBr) 2700–2500 (CO₂H), 1750 (NCO₂CH₃), 1710 (CO₂H) cm⁻¹; ¹H NMR (CDCl₃) δ3.68 (3H, s, NCO₂C$\underline{H}_3$), 4.51 (2H, s, OC$\underline{H}_2$CO2H), 4.60 (1H, bs, CO₂H), 4.95 (2H, s, C$\underline{H}_2$-oxazole), 6.77 (1H, dd, J=9 Hz, J'=2 Hz, aromatic $\underline{H}$), 6.94 (2H, m, aromatic $\underline{H}$), 7.15 to 7.40 (7H, m, aromatic $\underline{H}$), 7.45 to 7.65 (4H, m, aromatic $\underline{H}$); MS m/z 459 (MH⁺).

Anal. calcd. for C₂₆H₂₂N₂O₆. 0.5H₂O : C, 66.81; H, 4.96, N, 6.00; H₂O, 1.93. Found: C, 66.86; H, 4.82; N, 5.97; H₂O, 0.80%.

EXAMPLE 12

Methyl [3-[[(4,5-diphenyl-2-oxazolyl)methyl](ethoxycarbonyl) amino]phenoxy]acetate(12d)

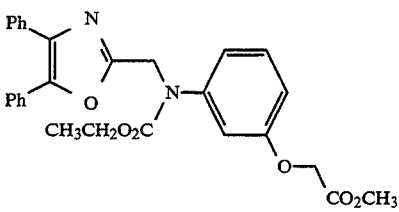

A solution of methyl [3-[(ethoxycarbonyl) amino]-phenoxy]acetate (4.10 g, 16 mmol) was dissolved in DMF (40 mL), NaH (0.94 g of a 50% dispersion in mineral oil, 19 mmol) added and the mixture stirred at room temperature for about 20 minutes. 2-Bromomethyl-4,5-diphenyl-oxazole (5.10 g, 16 mmol) in DMF (15 mL) was added dropwise and the mixture stirred at room temperature for about 3 hours. The mixture was diluted with H₂O, extracted with Et₂O and the combined extracts washed with H₂O. After drying over MgSO₄, the solvent was evaporated and the residue chromatographed twice on a column of silica gel using hexane/EtOAc (4:1) for the first column and CH₂Cl₂/MeOH (24:1) for the second to give methyl [3-[[(4,5-diphenyl-2-oxazolyl)methyl](ethoxycarbonyl)amino]phenoxy]acetate (1.50 g, 19%). IR (film) 1765, 1710 cm⁻¹; ¹H NMR (CDCl₃) δ1.22 (3H, t, J=8 Hz, OCH₂CH₃), 3.75 (3H, s, CO₂CH₃), 4.21 (2H, q, J=8 Hz, OCH₂CH₃), 4.47 (2H, s, OCH₂CO₂CH₃), 5.00 (2H, s, CH₂-oxazole), 5.28 (0.2H, s, CH₂Cl₂), 6.79 (1H, dd, J=9 Hz, J'=2 Hz, aromatic H), 7.05 (2H, m, aromatic H), 7.20 to 7.40 (7H, m, aromatic H), 7.50 to 7.70 (4H, m, aromatic H); MS m/z 487 (MH+).

Anal. calcd. for C₂₈H₂₆N₂O₆. 0.11CH₂Cl₂: C, 68.09; H, 5.33, N, 5.65. Found: C, 68.03; H, 5.22; N, 5.52%.

EXAMPLE 13

[3-[[(4,5-diphenyl-2-oxazolyl)methyl](ethoxycarbonyl)amino]phenoxy]acetic acid(13d)

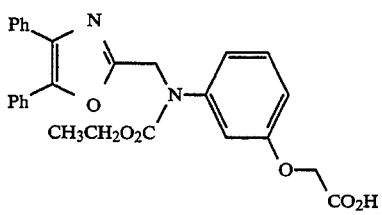

A mixture of methyl [3-[[(4,5-diphenyl-2-oxazolyl)methyl](ethoxycarbonyl)amino]phenoxy]acetate (0.90 g, 1.9 mmol), LiOH.H₂O (82 mg, 2 mmol) and 95% EtOH (25 mL) was stirred at room temperature for about 25 hours. The EtOH was evaporated, the residue diluted with H₂O and acidified with 2N HCl solution. Extraction with CH₂Cl₂ afforded an oil which was chromatographed first on a column of silica gel using CH₂Cl₂/MeOH (9:1) as eluent and subsequently on a column of silica gel using hexanes/EtOAc/AcOH (12:7:1) as eluent to give [3-[[(4,5-diphenyl-2-oxazolyl)methyl](ethoxycarbonyl)amino]phenoxy]acetic acid (0.70 g, 80%). IR (film) 3000, 1710 cm⁻¹; ¹H NMR (CDCl₃) δ1.22 (3H, t, J=8 Hz, OCH₂CH₃), 4.21 (2H, q, J=8 Hz, OCH₂CH₃), 4.55 (2H, s, OCH₂CO₂CH₃), 5.03 (2H, s, CH₂-oxazole), 6.79 (1H, dd, J=9 Hz, J'=2 Hz, aromatic H), 7.00 (2H, m, aromatic H), 7.20 to 7.40 (7H, m, aromatic H), 7.50 to 7.70 (4H, m, aromatic H), 10.49 (1H, bs, CO₂H); MS m/z 473 (MH+).

Anal. calcd. for C₂₇H₂₄N₂O₆. 1.2H₂O: C, 65.63; H, 5.39, N, 5.67. Found: C, 65.36; H, 4.81; N, 5.41%.

EXAMPLE 14

Methyl[3-[[(4,5-diphenyl-2-oxazolyl)methyl](n-propoxycarbonyl)amino]phenoxy]acetate(12e)

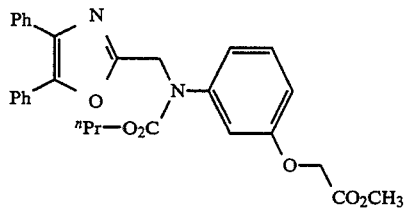

Isolated 4.75 g, 34% after chromatography on silica gel using hexanes/EtOAc (3:1) as eluent.

IR (film) 1765, 1710 cm⁻¹; ¹H NMR (CDCl₃) δ0.85 (3H, t, J=8 Hz, CH₂CH₃), 1.60 (2H, sextuplet, J=8 Hz, CH₂), 3.75 (3H, s, CO₂CH₃), 4.12 (2H, q, J=8 Hz, OCH₂CH₂), 4.60 (2H, s, OCH₂CO₂CH₃), 5.00 (2H, s, CH₂-oxazole), 6.80 (1H, dd, J=9 Hz, J'=2 Hz, aromatic H), 7.05 (2H, m, aromatic H), 7.20 to 7.40 (7H, m, aromatic H), 7.50 to 7.70 (4H, m, aromatic H); MS m/z 501 (MH+).

Anal. calcd. for C₂₉H₂₈N₂O₆.0.8H₂O: C, 67.64; H, 5.79, N, 5.44. Found: C, 67.62; H, 5.60; N, 5.21%.

EXAMPLE 15

3-[[(4,5-diphenyl-2-oxazolyl)methyl](n-propoxycarbonyl)amino]phenoxy]acetic acid(13e)

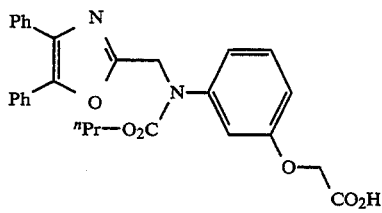

Isolated 1.95 g, 62% as a foam after repeated chromatography on silica gel using hexanes/EtOAc/AcOH (12:7:1) as eluent.

IR (film) 3000, 1710 cm⁻¹; ¹H NMR (CDCl₃) δ0.85 (3H, t, J=8 Hz, CH₂CH₃), 1.60 (2H, sextuplet, J=8 Hz, CH₂), 4.11 (2H, q, J=8 Hz, OCH₂CH₂), 4.56 (2H, s, OCH₂CO₂H), 5.00 (2H, s, CH₂-oxazole), 6.79 (1H, dd, J=9 Hz, J'=2 Hz, aromatic H), 7.02 (2H, m, aromatic H), 7.20 to 7.50 (7H, m, aromatic H), 7.50 to 7.70 (4H, m, aromatic H); MS m/z 487 (MH+).

Anal. calcd. for C₂₈H₂₆N₂O₆.0.3H₂O: C, 68.37 H, 5.45, N, 5.70. Found: C, 68.26; H, 5.46; N, 5.67%.

EXAMPLE 16

Methyl[3-[[(4,5-diphenyl-2-oxazolyl)methyl](i-propoxycarbonyl)amino]phenoxy]acetate (12f)

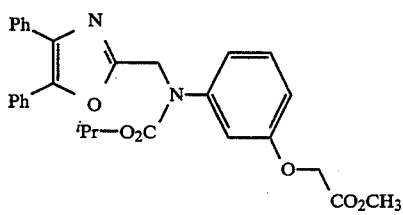

Isolated 6.0 g, 31% after chromatography on silica gel using hexanes/EtOAc (3:1) as eluent.

IR (film) 1765, 1740, 1710 cm$^{-1}$; $^1$H NMR (CDCl$_3$) δ1.21 (3H, d, J=8 Hz, CH(CH$_3$)), 3.75 (3H, s, CO$_2$CH$_3$), 4.60 (2H, s, OCH$_2$CO$_2$CH$_3$), 5.00 (2H, s, CH$_2$-oxazole), 5.05 (1H, m, OCH(CH$_3$)), 6.80 (1H, dd, J=9 Hz, J'=2 Hz, aromatic H), 7.05 (2H, m, aromatic H), 7.20 to 7.40 (7H, m, aromatic H), 7.50 to 7.70 (4H, m, aromatic H); MS m/z 501 (MH+).

Anal. calcd. for C$_{29}$H$_{28}$N$_2$O$_6$.0.88H$_2$O: C, 67.46; H, 5.80, N, 5.42. Found: C, 67.46; H, 5.48; N, 5.21%.

EXAMPLE 17

[3-[[(4,5-diphenyl-2-oxazolyl)methyl](i-propoxycarbonyl)amino]phenoxy]acetic acid (13f)

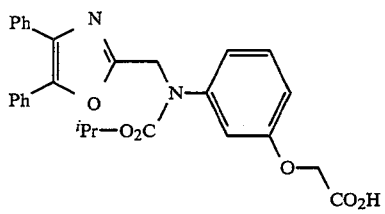

Isolated 1.70 g, 44% as a foam after repeated chromatography on silica gel using hexanes/EtOAc/AcOH (12:7:1) as eluent.

IR (film) 3450, 3000, 1710 cm$^{-1}$; $^1$H NMR (CDCl$_3$) δ1.21 (3H, d, J=8 Hz, CH(CH$_3$)$_2$), 4.56 (2H, s, OCH$_2$CO$_2$H), 4.99 (1H, quintuplet, J=7 Hz, CH(CH$_3$)$_2$), 5.06 (2H, s, CH$_2$-oxazole), 6.79 (1H, dd, J=9 Hz, J'=2 Hz, aromatic H), 7.02 (2H, m, aromatic H), 7.20 to 7.50 (7H, m, aromatic H), 7.50 to 7.70 (4H, m, aromatic H); MS m/z 487 (MH+).

Anal. calcd. for C$_{28}$H$_{26}$N$_2$O$_6$. 0.4H$_2$O: C, 68.11 H, 5.47, N, 5.67. Found: C, 68.08; H, 5.45; N, 5.48%.

EXAMPLE 18

5- (4,5-Diphenyl-2-oxazolyl) -2-pyrrolidinone (18)

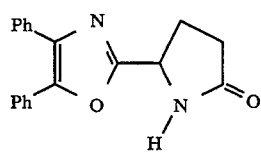

A mixture of benzoin (45.19 g, 0.21 mol), pyroglutamic acid (25.00 g, 0.19 tool), DCC (47.91 g, 0.23 mol), DMAP (catalytic quantity) and CH$_2$Cl$_2$ (600 mL) was stirred at room temperature. After about 7 hours, the mixture was filtered, concentrated and diluted with AcOH (650 mL). NH$_4$OAc (75.00 g, 0.97 mol) was added and the mixture heated at reflux for about 1.25 hours before being cooled, diluted with H$_2$O and extracted with CH$_2$Cl$_2$. The combined extracts were washed with H$_2$O (3 times), dried over Na$_2$SO$_4$ and concentrated in vacuo to give a yellow solid. Chromatography on a column of silica gel using a mixture of CHCl$_3$ and MeOH (99:1) as eluent afforded 5-(4,5-diphenyl-2-oxazolyl) -2-pyrrolidinone (42.58 g, 72%). An analytical sample was recystallised from CH$_2$Cl$_2$ and hexanes and had mp 145–147° C. IR (KBr)1700 (NH.CO) cm$^{-1}$; $^1$H NMR (DMSO-d$_6$) δ2.15–2.60 (4H, m, CH$_2$), 4.89 (1H, m, CHN), 7.10–7.70 (10H, m, aromatic H), 8.33 (1H, s, NH); MS m/z 305 (MH+).

Anal. calcd. for C$_{19}$H$_{16}$N$_2$O$_2$: C, 74.98 H, 5.30, N, 9.20. Found: C, 74.93; H, 5.40; N, 9.21%.

EXAMPLE 19

Methyl 2- (4,5-diphenyl-2-oxazolyl) -5-oxo-1-pyrrolidineoctanoate (19b)

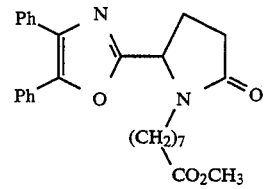

NaH (820 mg of a 50% dispersion, 17 mmol) was covered with DMF (80 mL) and 5-(4,5-diphenyl-2-oxazolyl)-2-pyrrolidinone (4.00 g, 13 mmol) added. The mixture was stirred at about 120° C. for about 15 minutes, cooled to room temperature and methyl 8-bromooctanoate (3.42 g, 14.5 mmol) added. The mixture was heated at about 110° C. for about 1 hour, cooled, diluted with 1N HCl and extracted with Et$_2$O (3 times). The combined extracts were washed with H$_2$O (3 times), dried over Na$_2$SO$_4$ and the solvent evaporated. The residual oil was chromatographed on a column of silica gel using Et$_2$O as eluent to afford methyl 2-(4,5-Diphenyl-2-oxazolyl)-5-oxo-l-pyrrolidineoctanoate (4.85 g, 80%) as an oil. IR (Film) 1740 (CO$_2$CH$_3$), 1695 (N.CO) cm$^{-1}$; 1H NMR (CDCl$_3$) δ1.18–1.60 (10H, m, CH$_2$), 2.20 (2H, t, J=7 Hz, CH$_2$CO$_2$CH$_3$), 2.30–2.55 (3H, m, CH$_2$ of ring), 2.73 (1H, m, CH$_2$ of ring), 3.00 (2H, m, NCH$_2$ of side chain), 3.61 (3H, s, CO$_2$CH$_3$), 4.86 (1H, m, CHN of ring), 7.25–7.40 (6H, m, aromatic H), 7.50–7.70 (4H, m, aromatic H), MS m/z 461 (MH+).

Anal. calcd. for C$_{28}$H$_{32}$N$_2$O$_4$.0.19 H$_2$O: C, 72.48; H, 7.04; N, 6.04; H$_2$O, 0.74. Found: C, 72.48, H, 7.00; N, 6.14; H$_2$O, 0.12%.

EXAMPLE 20

2- (4,5-diphenyl-2-oxazolyl) -5-oxo-1-pyrrolidineoctanoic acid (20b)

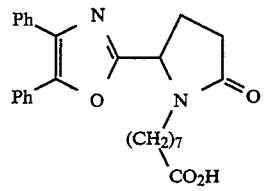

A mixture of methyl 2- (4,5-diphenyl-2-oxazolyl)-5-oxo-1-pyrrolidineoctanoate (3.60 g, 7.8 mmol), LiOH.-H$_2$O (986 mg, 24 mmol), MeOH (60 mL) and H$_2$O (10 mL) was stirred at room temperature. After about 45 minutes, the mixture was concentrated, diluted with 1N HCl solution and extracted with CH$_2$Cl$_2$. The combined extracts were dried over Na$_2$SO$_4$ and concentrated to leave an oil. Chromatography on a column of silica gel using a mixture of MeOH and CHCl$_3$ (1:1) as eluent furnished 2-(4,5-diphenyl-2-oxazolyl) -5-oxo-1-pyrrolidineoctanoic acid (1.76 g, 50%). IR (Film) 3600–2400 (CO$_2$H), 1725 (CO$_2$H), 1695 (N.CO) cm$^{-1}$; 1H NMR (CDCl$_3$) δ1.20–1.65 (10H, m, CH$_2$), 2.24 (2H, t, J=7.5 Hz, CH$_2$CO$_2$H), 2.30–2.60 (3H, m, CH$_2$ of ring), 2.75 (1H, m, CH$_2$ of ring), 3.03 (1H, m, NCH$_2$ of side chain), 3.60 (1H, quintuplet, J=7 Hz, NCH$_2$ of side chain), 4.90 (1H, m, NCH of ring), 5.26 (0.3H, s, CH$_2$Cl$_2$), 7.30–7.45 (6H, m, aromatic H), 7.50–7.65 (4H, m, aromatic H), 9.87 (1H, bs, CO$_2$H); MS m/z 447 (MH+).

Anal. calcd. for C$_{27}$H$_{30}$N$_2$O$_4$. 0.21 CH$_2$Cl$_2$: C, 70.43; H, 6.61; N, 6.04. Found: C, 70.43, H, 6.68; N, 6.22%.

EXAMPLE 21

Methyl 2- (4,5-diphenyl-2-oxazolyl)
-5-oxo-1-pyrrolidineheptanoate (19a).

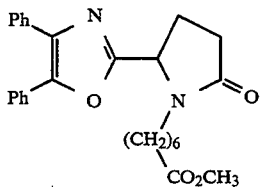

Isolated 4.40 g (75%) from 5-(4,5-diphenyl-2-oxazolyl)-2-pyrrolidinone (4.00 g, 13 mmol) using methyl 7-bromoheptanoate as the electrophile. IR (Film) 1740 (CO$_2$CH$_3$), 1700 (N.CO) cm$^{-1}$; $^1$H NMR (CDCl$_3$) δ1.20–1.65 (8H, m, CH$_2$), 2.22 (2H, t, J=7.5 Hz, CH$_2$CO$_2$CH$_3$), 2.35–2.55 (3H, m, CH$_2$ of ring), 2.72 (1H, m, CH$_2$ of ring), 3.00 (1H, m, NCH$_2$ of side chain), 3.58 (3H, s, CO$_2$CH$_3$), 4.86 (1H, m, CHN of ring), 7.30–7.40 (6H, m, aromatic H), 7.50–7.70 (4H, m, aromatic H), MS m/z 447 (MH+).

Anal. calcd. for C$_{27}$H$_{30}$N$_2$O$_4$. 0.175 H$_2$O: C, 72.12; H, 6.80; N, 6.23; H$_2$O, 0.70. Found: C, 72.12, H, 6.86; N, 6.17; H$_2$O, 0.01%.

EXAMPLE 22

2- (4,5-diphenyl-2-oxazolyl)
-5-oxo-1-pyrrolidineheptanoic acid (20a)

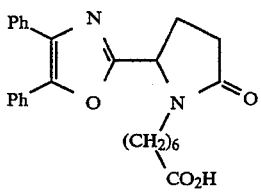

Isolated 1.43 g (49%). IR (Film) 3600–2400 (CO$_2$H), 1725 (CO$_2$H), 1700 (N.CO) cm$^{-1}$; $^1$H NMR (CDCl$_3$) δ1.20–1.70 (8H, m, CH$_2$), 2.25 (2H, t, J=7.5 Hz, CH$_2$CO$_2$H), 2.35–2.65 (3H, m, CH$_2$ of ring), 2.75 (1H, m, CH$_2$ of ring), 3.05 (1H, m, NCH$_2$ of side chain), 3.61 (1H, quintuplet, J=7 Hz, NCH$_2$ of side chain), 4.91 (1H, m NCH of ring), 5.26 (0.43H, s, CHCl$_2$), 7.30–7.45 (6H, m, aromatic H), 7.50–7.70 (4H, m, aromatic H), MS m/z 433 (MH+).

Anal. calcd. for C$_{26}$H$_{28}$N$_2$O$_4$. 0.3CH$_2$Cl$_2$: C, 68.97; H, 6.80; N, 6.12. Found: C, 69.01, H, 6.49; N, 6.18%.

EXAMPLE 23

Methyl 1-(3-hydroxyphenyl)-5-oxo-2pyrrolidinecarboxylate (23)

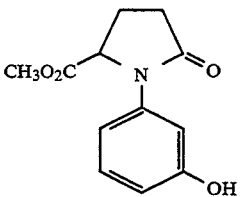

NaBH$_3$CN (11.55 g, 0.18 mol) was added to a stirred solution of 3-aminophenol (10.00 g, 0.09 mol) and 2-ketoglutaric acid (17.41 g, 0.12 mol) in MeOH (350 mL). After about 17 hours, 2-ketoglutaric acid (1.00 g, 7 mmol) was added and the mixture stirred for about 1 hour. cH$_2$SO$_4$ was added until pH=1 and the mixture heated to reflux. cH$_2$SO$_4$ (3 mL) was added after about 3 hours and then again about 1 hour later. The mixture was heated at reflux overnight, the solvent evaporated and the residue diluted with water and 10% Na$_2$CO$_3$ solution. The mixture was extracted with CH$_2$Cl$_2$, the extracts dried over Na$_2$SO$_4$ and concentrated to leave an oil that crystallized. This was dissolved in CH$_2$Cl$_2$ containing a small amount of MeOH and diluted with hexanes to give methyl 1-(3-hydroxyphenyl)-5-oxo-2-pyrrolidinecarboxylate (18.75 g, 87%). An analytical sample was prepared by recrystallizing a 1 g sample from a mixture of CH$_2$Cl$_2$ and hexanes to give 0.98 g of pure material, mp 125–127° C. IR (KBr) 3200 (OH), 1730 (CO$_2$Me), 1660 (CONH) cm$^{-1}$. $^1$H NMR (CDCl$_3$) δ2.16 (1H, m, CH.CH$_2$CO), 2.40–2.70 (2H, m, CH$_2$CO), 2.80 (1H, m, CH.CH$_2$CO), 3.72 (3H, s, CO$_2$CH$_3$), 4.75 (1H, dd, J=6 Hz, J'=3 Hz, CHCO$_2$CH$_3$), 6.54 (1H, dd, J=8 Hz, J'=2 Hz, aromatic H), 6.68 (1H, dd, J=8 Hz, J'=2 Hz, aromatic H), 7.15 (1H, t, J=8 Hz, aromatic H meta to OH), 7.73 (1H, t, J=2 Hz, aromatic H ortho to N and OH), 8.35 (1H, bs, OH); $^{13}$C NMR (CDCl$_3$) δ22.97, 31.11, 52.73, 61.83, 109.21, 110.78, 113.20, 129.70, 138.58, 157.38, 172.04, 175.47; MS m/z 236 (MH+).

Anal. calcd. for C$_{12}$H$_{13}$NO$_4$: C, 61.27; H, 5.57; N, 5.95. Found: C, 61.07; H, 5.51, N, 5.81%.

EXAMPLE 24

1-(3-Hydroxyphenyl)-5-oxo-2-pyrrolidinecarboxylic acid (24)

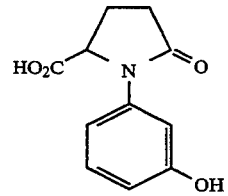

A mixture of methyl 1-(3-hydroxyphenyl)-5-oxo-2-pyrrolidinecarboxylate (10.00 g, 42 mmol), LiOH.H$_2$O (5.36 g, 128 mmol), MeOH (200 mL) and H$_2$O (50 mL) was stirred at room temperature for about 1 hour. The MeOH was removed in vacuo and the residue diluted with H$_2$O and 2N HCl solution to pH=1. The solid was filtered off, dried in air and suspended in hot CH₃CN (200 mL). Filtration gave 1-(3-hydroxyphenyl)-5-oxo-2-pyrrolidinecarboxylic acid (8.06 g, 85%), mp 183–185° C. IR (KBr) 3600–2300 (OH), 1710 (CO$_2$H), 1695 (CONH) cm$^{-1}$. $^1$H NMR (DMSO-d$_6$/CDCl$_3$) δ2.05 to 2.15 (1H, m, pyrrolidine ring H), 2.30–2.50 (3H, m, pyrrolidine ring H), 4.58 (1H, dd, J=9 Hz, J'=2 Hz, CHCO$_2$H), 6.52 (1H, dd, J=8 Hz, J'=2 Hz, aromatic H), 6.81 (1H, dd, J=8 Hz, J'=2Hz, aromatic H), 7.02 to 7.08 (2H, m, aromatic H), 9.16 (1H, bs, OH); MS m/z 222 (MH+).

Anal. calcd. for C$_{11}$H$_{11}$NO$_4$: C, 59.73; H, 5.01; N, 6.33. Found: C, 59.84; H, 5.01, N, 6.43%.

EXAMPLE 25

5-(4,5-Diphenyl-2-oxazolyl)-1-(3-hydroxyphenyl)-2-pyrrolidine (25)

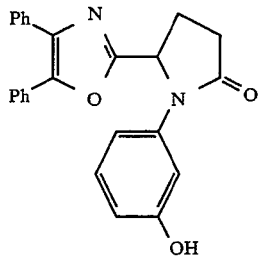

Sodium (1.30 g, 56 mg atom) was dissolved in EtOH (250 mL) and 1-(3-hydroxyphenyl)-5-oxo-2-pyrrolidinecarboxylic acid (12.50 g, 56 mmol) added. The mixture was heated at reflux for about 10 minutes, cooled, cH$_2$SO$_4$ (8 drops) added followed by desyl bromide (15.55 g, 56 mmol). The mixture was heated at reflux for about 5 hours, cooled and concentrated in vacuo. Acetic acid (180 mL) and NH$_4$OAc (21.77 g, 0.28 mol) was added and the mixture heated to reflux. After about 1 hour, the solution was cooled, diluted with H$_2$O and extracted with CH$_2$Cl$_2$. The combined extracts were washed with H$_2$O, dried over Na$_2$SO$_4$ and concentrated to leave a solid. Recrystallization from CH$_2$Cl$_2$/hexanes afforded 5-(4,5-diphenyl-2-oxazolyl)-1-(3-hydroxyphenyl)-2-pyrrolidine (18.20 g, 81%), mp 183–185° C. IR (KBr) 1675 (CONH), 1220 (C-OH) cm$^{-1}$. $^1$H NMR (DMSO-d$_6$) δ2.25 to 2.35 (1H, m, pyrrolidine ring H), 2.45–2.95 (3H, m, pyrrolidine ring H), 5.65 (1H, dd, J=8 Hz, J'=3 Hz, CH-oxazole), 6.56 (1H, dd, J=8 Hz, J'=2 Hz, aromatic H), 6.93 (1H, dd, J=8 Hz, J' =2 HZ, aromatic H), 7.10 to 7.20 (2H, m, aromatic H), 7.30 to 7.65 (10H, m, aromatic H), 9.55 (1H, bs, OH); MS m/z 397 (MH+).

Anal. calcd. for C$_{25}$H$_{20}$N$_2$O$_3$.0.25H$_2$O: C, 74.91; H, 5.11; N, 6.99; H$_2$O, 1.10. Found: C, 74.90; H, 5.09, N, 6.93; H$_2$O, 0.10%.

EXAMPLE 26

Methyl [3-[2-(4,5-diphenyl-2-oxazolyl)-5-oxo-1-pyrrolidinyl]-phenoxy]acetate (26)

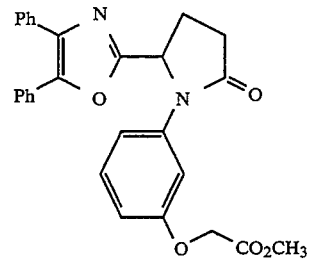

A mixture of 5-(4,5-diphenyl-2-oxazolyl)-1-(3-hydroxyphenyl)-2-pyrrolidine (5.00 g, 12 mmol), methyl bromoacetate (2.02 g, 1.25 mL, 13 mmol), pulverized K$_2$CO$_3$ (1.91 g, 13 mmol) and CH$_3$CN (100 mL) was heated at reflux for about 75 minutes. The mixture was cooled, filtered and concentrated to leave an oil. Chromatography on a coloumn of silica gel using a mixture of Et$_2$O and hexanes (4:1) as eluent gave methyl [3-[2-(4,5-diphenyl-2-oxazolyl)-5-oxo-1-pyrrolidinyl]-phenoxy]acetate (5.91 g, 100%) as an oil. IR (film) 1760 (CO$_2$Me), 1710 (CONH) cm$^{-1}$. $^1$H NMR (CDCl$_3$) δ2.40 to 2.55 (1H, m, pyrrolidine ring H), 2.60–2.75 (2H, m, pyrrolidine ring H), 2.90 to 3.05 (1H, m, pyrrolidine ring H), 3.74 (3H, s, CO$_2$CH$_3$), 4.59 (2H, s, OCH$_2$), 5.43 (1H, dd, J=8 Hz, J'=3Hz, CH-oxazole), 6.72 (1H, dd, J=8Hz, J'=2 Hz, aromatic H), 7.10 (1H, dd, J=8 Hz, J'=2 Hz, aromatic H), 7.15 to 7.30 (2H, m, aromatic H), 7.35 to 7.40 (6H, m, aromatic H), 7.50 (2H, m, aromatic H), 7.60 (2H, m, aromatic H), MS m/z 469 (MH+).

Anal. calcd. for C$_{28}$H$_{24}$N$_2$O$_5$: C, 71.78; H, 5.16; N, 5.98. Found: C, 71.70; H, 5.19, N, 5.83%.

EXAMPLE 27

[3-[2-(4,5-diphenyl-2-oxazolyl)-5-oxo-1pyrrolidinyl]-phenoxy]acetic acid (27)

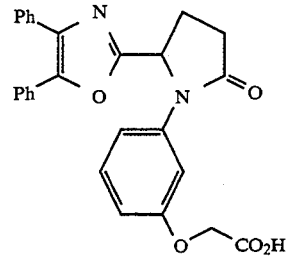

A mixture of methyl [3-[2-(4,5-diphenyl-2-oxazolyl)-5-oxo-1-pyrrolidinyl]phenoxy]acetate (4.60 g, 9.8 mmol), LiOH.H$_2$O (1.25 g, 29 mmol), MeOH (60 mL) and H$_2$O (15 mL) was stirred at room temperature for about 15 minutes. The MeOH was evaporated and the residue diluted with H$_2$O and 2N HCl until pH=1. Filtration gave a white solid that was taken up in CH$_2$Cl$_2$ and diluted with hexane. Evaporation of the solvent left [3-[2-(4,5-diphenyl-2-oxazolyl)-5-oxo-1-pyrrolidinyl]phenoxy]acetic acid as an amorphous solid (3.00 g, 67%), mp 75–90° C. IR (KBr) 1740 (CO$_2$H), 1710 (CONH) cm$^{-1}$. $^1$H NMR (CDCl$_3$) δ0.86 (3H, t, J=8 Hz, CH$_3$ of hexanes), 1.27 (4H, m, CH$_2$ of hexanes), 2.35 to 2.50 (1H, m, pyrrolidine ring H), 2.55–2.80 (2H, m, pyrrolidine ring H), 2.90 to 3.05 (1H, m, pyrrolidine ring H), 4.60 (2H, s, OCH$_2$), 5.59 (1H, dd, J=8 Hz, J'=3 Hz, CH-oxazole), 6.70 (1H, dd, J=8 Hz, J'=2 Hz, aromatic H), 7.08 (1H, dd, J=8 Hz, J'=2 Hz, aromatic H), 7.15 to 7.45 (8H, m, aromatic H), 7.44 to 7.50 (2H, m, aromatic H), 7.50 (2H, m, aromatic H), 7.56 (2H, m, aromatic H), 8.74 (1H, bs, CO$_2$H); MS m/z 455 (MH+).

Anal. calcd. for C$_{27}$H$_{22}$N$_2$O$_5$0.2C$_6$H$_{14}$.0.3H$_2$O: C, 70.99; H, 5.37; N, 5.87; H$_2$O, 1.13. Found: C, 70.97; H, 5.35, N, 5.61; H$_2$O, 1.15%.

We claim:

1. A compound of the formula

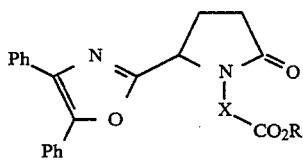

Formula II wherein
R is H or C$_1$–C$_5$ lower alkyl,
X is (CH$_2$)$_n$ or para or meta substituted phenyl wherein the substituent is OR$^2$,
R$^2$ is C$_1$–C$_5$ alkyl, and
n is an integer of 4 to 8, or
a pharmaceutically acceptable salt thereof.

2. The compound of claim 1 which is methyl 2-(4,5-diphenyl-2-oxazolyl)-5-oxo-1-pyrrolidineoctanoate.

3. The compound of claim 1 which is 2-(4,5-diphenyl-2-oxazolyl)-5-oxo-1-pyrrolidineoctanoic acid.

4. The compound of claim 1 which is methyl 2-(4,5-diphenyl-2-oxazolyl)-5-oxo-1-pyrrolidineheptanoate.

5. The compound of claim 1 which is 2-(4,5-diphenyl-2-oxazolyl)-5-oxo-1-pyrrolidineheptanoic acid.

6. The compound of claim 1 which is methyl [3-[2-(4,5-diphenyl-2-oxazolyl)-5-oxo-1-pyrrolidinyl]-phenoxy]acetate.

7. The compound of claim 1 which is [3-[2-(4,5-diphenyl-2-oxazolyl)-5-oxo-1-pyrrolidinyl]phenoxy]acetic acid.

* * * * *